United States Patent [19]

Champetier

[11] Patent Number: 4,808,813
[45] Date of Patent: Feb. 28, 1989

[54] SELF CONTAINED SURFACE CONTAMINATION SENSOR FOR DETECTING EXTERNAL PARTICULATES AND SURFACE DISCONTINUITIES

[75] Inventor: Robert J. Champetier, Torrance, Calif.

[73] Assignee: Hughes Aircraft Company, Los Angeles, Calif.

[21] Appl. No.: 859,563

[22] Filed: May 5, 1986

[51] Int. Cl.[4] .................. H01J 5/16; G01N 21/16
[52] U.S. Cl. ..................... 250/227; 250/223 B; 356/239
[58] Field of Search ............ 250/223 B, 227, 572; 356/239, 240

[56] References Cited

U.S. PATENT DOCUMENTS

| | | | |
|---|---|---|---|
| 3,328,000 | 6/1967 | Rottmann | 250/223 B |
| 3,394,263 | 7/1968 | Baker | 250/223 B |
| 3,894,806 | 7/1975 | Remy et al. | 250/223 B |
| 3,947,131 | 3/1976 | Karl | 356/209 |
| 4,297,032 | 10/1981 | Temple | 356/239 |
| 4,468,120 | 8/1984 | Tanimoto et al. | 356/239 |
| 4,652,745 | 3/1987 | Zanardelli | 250/227 |

FOREIGN PATENT DOCUMENTS

| | | |
|---|---|---|
| 3235590 | 3/1984 | Fed. Rep. of Germany . |
| 60-13247 | 1/1985 | Japan . |
| 898828 | 6/1962 | United Kingdom . |
| 2076962 | 12/1981 | United Kingdom . |

OTHER PUBLICATIONS

IBM Tech. Discl. Bull.; "Advanced Defect Detection System"; vol. 27; No. 12; May 1985; pp. 6999-7001.

Primary Examiner—David C. Nelms
Assistant Examiner—Stephone B. Allen
Attorney, Agent, or Firm—Lewis B. Sternfels; A. W. Karambelas

[57] ABSTRACT

Contamination, either in the form of particulate matter (46), e.g., dust and non-wetting liquid, or surface discontinuities (48), such as a smooth film or cratering, is collected on an explosed glass plate (12). Illumination at an angle incident with respect to a surface (14) of the glass plate causes the particulate matter to scatter light. A further light source illuminates the inside volume of the glass, causing light to scatter from the surface discontinuities. Either source of light scattering is detected by an optically sensitive detector (18) positioned beneath the glass plate. A bandpass filter (24) between the glass plate and the detector rejects spurious radiation.

15 Claims, 3 Drawing Sheets

SELF CONTAINED SURFACE CONTAMINATION SENSOR FOR DETECTING EXTERNAL PARTICULATES AND SURFACE DISCONTINUITIES

BACKGROUND OF THE INVENTION

1. Field of the Invention

The present invention relates to the detection of contamination in or on the surface of an optical element, in the respective form of surface discontinuities and particulate matter. By "discontinuities" is meant molecular matter which wets or craters the surface to form a greater than point contact or surface irregularity. By "particulate matter" is meant essentially a point contact with the surface. the difference between the two is primarily one of detectability, because both deleteriously affect the optical quality of the element.

2. Description of Related Art and Background Considerations

High quality, precision optical equipment often cannot perform to its optimum capabilities when its surfaces are contaminated. For example, an increased requirement of LWIR (long wave infrared) Space Surveillance Sensors is to detect low-radiance targets in the presence of intensive out-of-field sources, such as the earth and sun. This requirement places increasingly higher demands on system off-axis rejection capabilities, thus requiring very low scatter surfaces to be used for critical elements of the optical train. Particulate contamination, which is deposited on mirrors, filters and/or baffles during fabrication, sensor testing, storage, launch, deployment or operation, significantly raises the quantity of scattered energy falling on the focal plane, thereby causing unacceptable signal to noise performance. Contamination due to molecular outgassing, corrosion or pitting causes greater scatter internal to the sensor's optics. When deposited on the sensor's external surfaces, molecular contamination causes a degradation of the thermal control properties. The latter can affect sensor performance indirectly by lowering detector efficiency or by causing electronic malfunctions due to increased operating temperatures. Internal molecular contamination can also be so severe as to affect system throughput by decreasing the efficiency of key optics by severe scattering losses, bulk absorption or thin film interference.

The only known contamination detector is a photometer manufactured by Saab Aktienbolaget. It is useful for detecting only particulate matter. That device uses black glass witness samples which, once exposed, are placed in the photometer. The photometer comprises a low power microscope with a light meter. Because it requires a black glass witness sample, it requires that the sample plate be removed from the environment where the sample was obtained, and then read out at a remote location to record the particulate matter level. It is also incapable of detecting such surface discontinuities as craters or molecular deposits, which wet a surface of an optical element.

SUMMARY OF THE INVENTION

The present invention overcomes and avoids these and other problems by sensing and detecting both particulate matter and surface irregularities within a self-contained package and on-scene within the contaminating environment. Surface discontinuities are sensed by directing radiation from within the optical element to the exposed surface. Particulate matter is sensed by radiation directed externally at a grazing angle to the surface. While the scattering from both the surface discontinuities and the particulate matter can be obtained by separate detectors, it is preferred that a single detector be so used. To distinguish between particulate matter and surface discontinuities contamination, the external and internal sources of radiation may be alternatively applied. To prevent extraneous radiation from providing erroneous detection, a bandpass filter is positioned between the surface and the detector.

Several aims, advantages and objectives are derived from the present invention. Both particulate matter and surface discontinuities can be detected, with discrimination therebetween. The sensing and detection is obtainable by both a built-in light or self-contained source and detection system. Being self contained, it is possible to obtain sensing and detection in a wide range of environments, such as within hard to reach surfaces or with remotely positioned optical devices, such as spaced telescopes or other hardware, or on external spacecraft surfaces, or in corrosive or abrasive environments. Other environments include the interior of any optical device whether space or earth bound. Monitoring of particulate matter or surface discontinuities can be continuous or, if desired, through occasional interrogation, in order to obtain accumulative reading. All sensing and detection is achievable without the need to open or even touch the device, and without having to await processing at a location remote from where the sensing and detecting is taking place.

Other aims, objectives and advantages, as well as a more complete understanding of the present invention will appear from the following explanation of an exemplary embodiment and the accompanying drawings thereof.

BRIED DESCRIPTION OF THE DRAWINGS

DESCRIPTION OF THE PREFERRED EMBODIMENT

Figure 1:
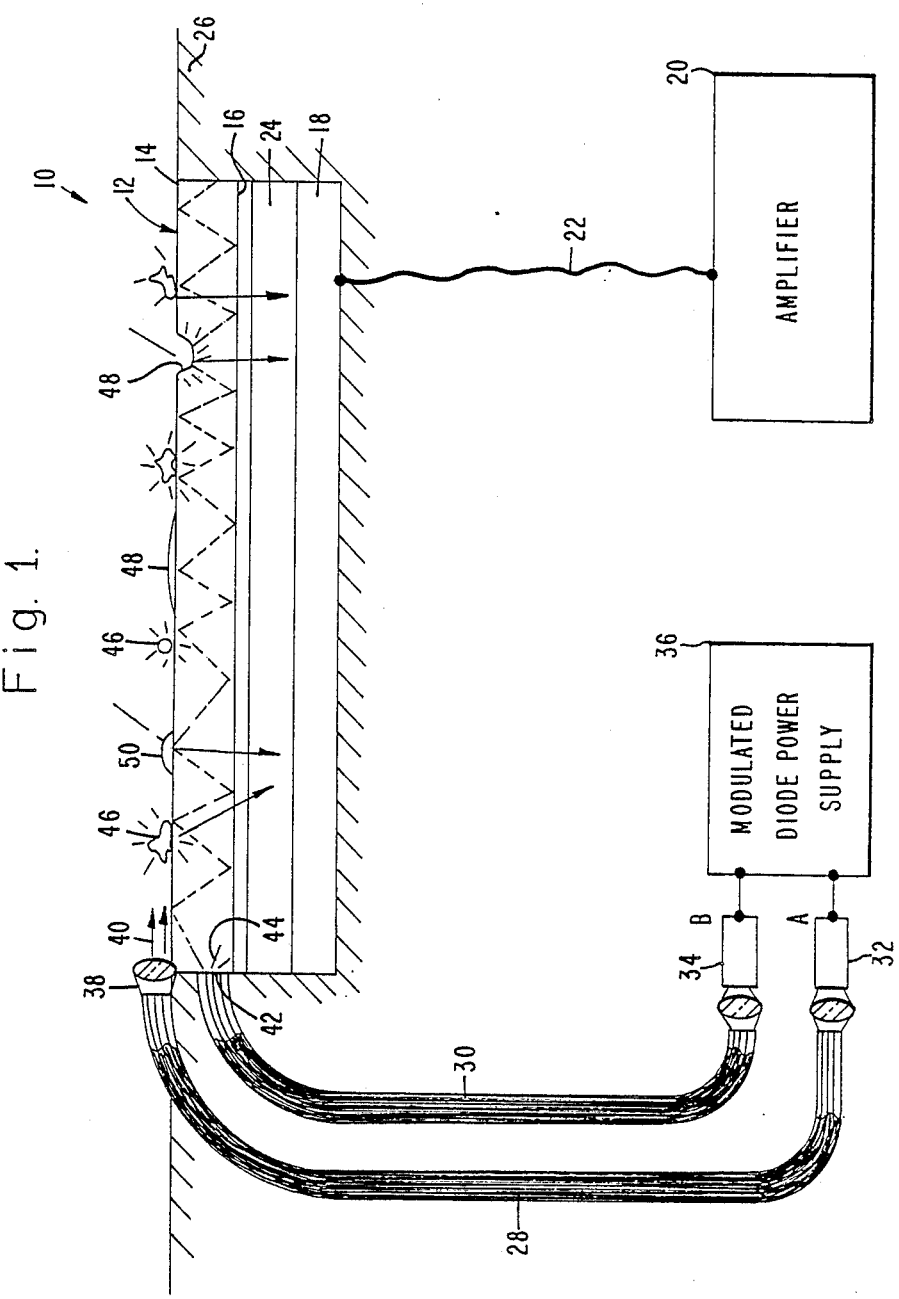
FIG. 1 is a side view of the present invention.

Accordingly, a monitor 10 comprises a plate 12 having one surface 14 which is exposed to the environment and a second surface 16 which faces a detector 18. Plate 12 is formed of a material, e.g., glass, which is capable of enabling illuminating electromagnetic radiation to propagate therethrough. The detector is coupled to processing and display electronic equipment 20 by a coupling 22. Positioned between detector 18 and surface 16 is a bandpass filter 24.

Plate 12, bandpass filter 24, and detector 18 may be mounted within a suitable mounting device 26.

Optically coupled to plate 12 are a pair of fiber optic bundles 28 and 30. Both bundles are coupled at their ends to laser diodes 32 and 34 which, in turn, are commonly coupled to a modulated diode power supply 36. In its preferred embodiment, power supply 36 is disposed to activate only one laser diode at a time so that electro-magnetic radiation in the form of laser radiation is directed to one or the other waveguide 28 or 30.

Figure 2:
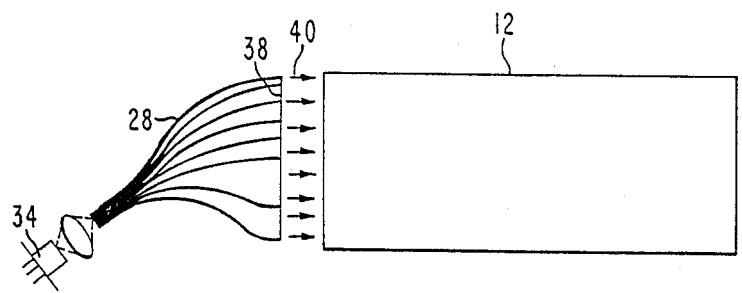
FIG. 2 is a plan or top view of the invention.

At their other ends, waveguides 28 and 30 are coupled to plate 12. End 38 of waveguide 28 is fanned out, as shown in FIG. 2, and directed externally and at an angle to surface 14 of plate 12 so that its radiation, as depicted by arrows 40, is directed parallel or at any other convenient angle to surface 14. Waveguide 30 is coupled at its end 42, which is fanned out similarly as shown in FIG. 2, to plate 12 in such a manner that its radiation, as designated by lines 44, traverses through the interior of the plate.

Radiation 40 and 44 are disposed to sense different types of contamination. As shown, various types of contamination include particulate matter, generally designated by indicia 46 and surface discontinuities, such as are designated by indicia 48. Examples of particulate matter include dust and non-wetting liquids, respectively illustrated as a particle having an irregular surface or a generally spherical drop. Examples of surface discontinuities include a smooth film which wets a large area of the surface, or cratering. A liquid which may be in contact with the surface to a greater or lesser extent may include a liquid drop 50 which has characteristics of both particulate matter and a surface discontinuity.

In general, external radiation will illuminate or be deflected from particulate matter 46, while internal radiation 44 will not be appreciably affected thereby. Alternatively, surface discontinuities 48 generally do not affect surface directed radiation 40, but significantly affect internal radiation 44. Thus, the manner in which the particulate matter or the surface discontinuities affect the respective radiations 40 and 44, provides an indicia of the condition of surface 14. Such indicia is detected by detector 18. However, in order not to permit spurious radiation, such as from sunlight, from erroneously affecting the detection, a bandpass filter 24 is used to permit radiation 40 and 44 to pass through, but to reject other radiation. The radiation striking detector 18 is transmitted to electronic equipment 20 for appropriate processing.

Figure 3:
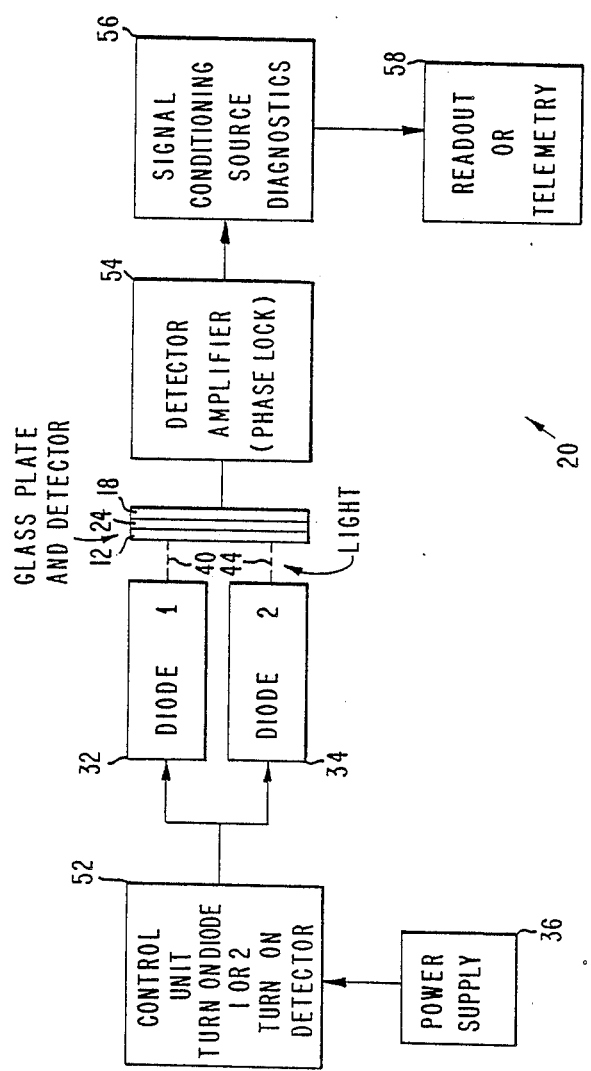
FIG. 3 is a schematic of the electronics useful in operating the invention.

FIG. 3 schematically illustrates the above process. Power supply 36 actuates one of diodes 32 and 34 as controlled by a control unit 52. Laser radiation 40 or 44 from respective diodes 32 and 34 is directed to plate 12 and passes through filter 24 to detector 18, for supply to electronic equipment 20. Electronic equipment 20 may comprise a detector amplifier 54, such as a phase lock amplifier, whose signal is then directed to signal conditioning and source diagnostics circuitry 56 which, in turn, is coupled to readout or telemetry 58.

While the preferred radiation is laser radiation, any other optical means of illuminating plate 12 is suitable, providing that the exciting source produces grazing incidence light. In addition, the electronics can be either direct current or alternating current. Modulating a diode source is convenient, such as by use of a gallium arsenide laser diode. This permits the detector to be sensed by phase lock detection. Suitable detection is obtainable by conventional solar cells.

In addition, plate 12 need not be of glass, which works well with a laser diode/silicon pair at 850 nanometers, just past the visible range into the infrared; any other combination of source/detector pair with a suitable plate and bandpass filter is acceptable. Illustrative is an infrared diode source, a silicon or germanium plate, and an infrared detector.

Although the invention has been described with reference to a particular embodiment thereof, it should be realized that various changes and modifications may be made therein without departing from the spirit and scope of the invention.

What is claimed is:

1. Apparatus self contained with an optical element for detecting both surface discontinuities associated with the optical element and particulate matter on a surface of the optical element, comprising:
   means for generating electromagnetic radiation positioned adjacent the optical element;
   a pair of optical waveguides coupled to the generating means for receiving the radiation and coupled to the optical element and positioned with respect thereto for directing the radiation respectively into the interior thereof and at an angle to the surface thereof, respectively for sensing the surface discontinuities and the particulate matter and thereby for providing respective indicia thereof; and
   means for detecting the respective indicia.

2. Apparatus according to claim 1 in which said generating means comprises a source of laser radiation as the electromagnetic radiation coupled to said waveguides.

3. Apparatus according to claim 1 further comprising a bandpass filter between the optical element and said detecting means for limiting detection to the indicia.

4. Apparatus according to claim 1 in which said waveguides comprise fiber optic bundles coupled to the optical element.

5. Apparatus according to claim 1 in which said generating means comprises a source of the radiation alternatively coupled to said waveguides for identifying the respective particulate matter indicia and the discontinuities indicia.

6. Apparatus according to claim 2 in which said source comprises a laser diode and a modulated diode power supply coupled thereto.

7. Apparatus according to claim 6 further comprising a bandpass filter between the optical element and said detecting means for limiting detection to the radiation.

8. Apparatus according to claim 5 in which said source comprises laser diodes respectively coupled to said waveguides and a modulated diode power supply coupled to said diodes for providing laser radiation as the electromagnetic radiation.

9. Apparatus according to claim 8 further comprising a bandpass filter between the optical element and said detecting means for limiting detection to the radiation.

10. Apparatus self contained with an optical element for detecting particulate matter and discontinuities respectively on and associated with a surface of the optical element comprising:
    means for sensing both the particulate matter and the discontinuities respectively from both sides of the surface, externally and internally of the optical element for providing indicia thereof; and
    means for detecting the indicia.

11. Apparatus for detecting contaminants associated with an optical element surface comprising:
    means for sensing the contaminants and for providing indicia of their presence in which the indicia comprises electromagnetic radiation of known frequency;
    means physically coupled to the surface for detecting the indicia; and
    a bandpass filter between said detecting means and the surface for limiting passage therethrough to the radiation.

12. A method for detecting both surface discontinuities associated with an optical element and particulate matter thereon, comprising the steps of:
   applying electromagnetic radiation to the discontinuities from without the element for respectively sensing the discontinuities and the particulate matter for providing respective indicia thereof; and
   detecting the respective indicia.

13. A method according to claim 12 in which said detecting step comprises the step of alternately detecting the discontinuities indicia and the particulate matter indicia for discriminating one from the other.

14. A method according to claim 13 further comprising the step of filtering out radiation extraneous to the electromagnetic radiation prior to said detecting step.

15. A method for detecting contamination of a surface of an optical element comprising the steps of:
   sensing the contamination from both sides of the surface, externally and internally of the optical element for providing indicia thereof; and
   detecting the indicia contemporaneously with said sensing step.

* * * * *